United States Patent
Kamen et al.

(10) Patent No.: US 8,386,015 B2
(45) Date of Patent: Feb. 26, 2013

(54) INTEGRATION OF MICRO AND MACRO INFORMATION FOR BIOMEDICAL IMAGING

(75) Inventors: Ali Kamen, Princeton, NJ (US); Fred S. Azar, Oakland, NJ (US); John V. Frangioni, Wayland, MA (US)

(73) Assignees: Siemens Aktiengesellschaft, München (DE); Beth Israel Deaconess Medical Center, Boston, MA (US)

( * ) Notice: Subject to any disclaimer, the term of this patent is extended or adjusted under 35 U.S.C. 154(b) by 167 days.

(21) Appl. No.: 12/604,504

(22) Filed: Oct. 23, 2009

(65) Prior Publication Data

US 2011/0040169 A1    Feb. 17, 2011

Related U.S. Application Data

(60) Provisional application No. 61/108,643, filed on Oct. 27, 2008.

(51) Int. Cl.
*A61B 5/00* (2006.01)
(52) U.S. Cl. ......... 600/411; 600/425; 600/427; 382/128
(58) Field of Classification Search .................. 600/411, 600/425, 427, 407; 382/128
See application file for complete search history.

(56) References Cited

U.S. PATENT DOCUMENTS

| | | | |
|---|---|---|---|
| 6,869,397 B2 * | 3/2005 | Black et al. ................ | 600/168 |
| 7,162,292 B2 * | 1/2007 | Ohno et al. ................ | 600/407 |
| 7,831,075 B2 * | 11/2010 | Wilson et al. .............. | 382/128 |
| 7,872,759 B2 * | 1/2011 | Tearney et al. ............. | 356/479 |
| 2006/0159367 A1 * | 7/2006 | Zeineh et al. .............. | 382/276 |
| 2008/0241873 A1 * | 10/2008 | Bornhop et al. ............. | 435/29 |
| 2009/0012369 A1 * | 1/2009 | Robinson et al. ............ | 600/182 |
| 2009/0035218 A1 * | 2/2009 | Ross et al. ................ | 424/9.1 |
| 2009/0213214 A1 * | 8/2009 | Yamada .................... | 348/80 |
| 2010/0121172 A1 * | 5/2010 | Ladic et al. ............... | 600/407 |
| 2010/0177185 A1 * | 7/2010 | Woerlein et al. ............ | 348/77 |
| 2011/0116694 A1 * | 5/2011 | Gareau .................... | 382/128 |
| 2011/0285838 A1 * | 11/2011 | Kishima et al. ............. | 348/79 |
| 2012/0140999 A1 * | 6/2012 | Kishima ................... | 382/128 |
| 2012/0147359 A9 * | 6/2012 | Stetten et al. .............. | 356/73 |
| 2012/0208184 A1 * | 8/2012 | Ragan .................... | 435/6.11 |

OTHER PUBLICATIONS

U.S. Appl. No. 12/369,847, filed Feb. 12, 2009.
Marina Chicurel, "Databasing the brain", Nature International Weekly Journal of Science, Aug. 24, 2000, Nature 506, 822-825.
"LONI Atlases", LONI Laboratory of Neuro Imaging, UCLA, http://www.loni.ucla.edu/Altases/.
Wieslaw L. Nowinski (Hrsg.), "The Cerefy Clinical Brain Atlas", Enhanced Edition with Surgical Planning and Intraoperative Support, CD-ROM. 2005, $2^{nd}$ Edition.
Google Earth, "Explore, Search, and Discover", http://earth.google.com.

(Continued)

*Primary Examiner* — Brian Casler
*Assistant Examiner* — Amanda Lauritzen
(74) *Attorney, Agent, or Firm* — Donald B. Paschburg

(57) ABSTRACT

Macroscopic imaging data, such as from a CT, MR, PET, or SPECT scanner, is obtained. Microscopic imaging data of at least a portion of the same tissue is obtained. To align the microscopic imaging data with the macroscopic imaging data, intermediate data is also obtained. For example, photographic data is acquired at an intermediary stage of a process of preparing tissue for microscopic scan. The macroscopic and microscopic data are registered to the intermediary photographic data. Once registered to the intermediary data, the spatial relationship between the macroscopic and microscopic data is known and may be used for imaging or quantification.

12 Claims, 2 Drawing Sheets

OTHER PUBLICATIONS

Brain Maps.org, "Explore the Brain like never before", http://brainmaps.org/.

Grady, L., *Random walks for image segmentation*. IEEE Trans Pattern Anal Mach Intell, 2006. 28: 1768-83.

Grady, L., *Fast, quality, segmentation of large volumes—isoperimetric distance trees*. Proceedings of ECCV 2006, May, Graz, Austria, Springer., 2006. 3: 449-462.

Sinop, A.K. and L. Grady, *A seeded image segmentation framework unifying graph cuts and random walker which yields a new algorithm*. ICCV 2007, Rio de Janeiro, Brazil, Oct. 14-20, 2007. Accepted.

Besl, P.J. and D. McKay, *A method for registration of 3-d shapes*. IEEE Trans. Pat. Anal. and Mach. Intel., 1992. 14: 239-256.

Grady, L., *Fast Approximate Random Walker Segmentation Using Eigenvector Precomputation*. Proc. of CVPR 2008.

\* cited by examiner

INTEGRATION OF MICRO AND MACRO INFORMATION FOR BIOMEDICAL IMAGING

RELATED APPLICATIONS

The present patent document claims the benefit of the filing date under 35 U.S.C. §119(e) of Provisional U.S. Patent Application Ser. No. 61/108,643, filed Oct. 27, 2008, which is hereby incorporated by reference.

FEDERALLY SPONSORED RESEARCH OR DEVELOPMENT

The U.S. Government has a paid-up license in this invention and the right in limited circumstances to require the patent owner to license others on reasonable terms as provided by the terms of grant no. 1R01CA134493-01A1 awarded by NIH.

BACKGROUND

The present embodiments relate to biomedical imaging, such as medical diagnostic, pharmaceutical, or clinical imaging. Different types of medical imaging modes are available. For example, medical imaging includes x-ray, ultrasound, computed tomography (CT), magnetic resonance (MR), positron emission (PET), single photon emission (SPECT), and optical imaging. Other medical imaging includes microscopy. A tissue sample is scanned, such as taking an optical picture, using magnification available with a microscope.

The biomedical image data may be used to assist medical professionals, such as researchers. Macroscopic scan data, such as MR, CT, PET, or SPECT, provides one source of information. Microscopic data provides another source of information. To obtain microscopic data, tissue is removed from a patient, encased, frozen, sliced, and mounted to slides. This process distorts the tissue. It is difficult to spatially correlate the macroscopic data with the microscopic data. Instead, the medical professionals separately view each type of data.

BRIEF SUMMARY

By way of introduction, the preferred embodiments described below include methods, systems, instructions, and computer readable media for biomedical imaging or other study. Macroscopic imaging data, such as from a CT, MR, PET, or SPECT scanner, is obtained. Microscopic imaging data of at least a portion of the same tissue is obtained. To align the microscopic imaging data with the macroscopic imaging data, intermediary data is also obtained. For example, the photographic data is acquired at an intermediary stage of the process of preparing tissue for microscopic scan. The macroscopic and microscopic data are registered to the intermediary photographic data. Once registered to the intermediary data, the spatial relationship between the macroscopic and microscopic data is known and may be used for cross validation or quantification.

In a first aspect, a method is provided for biomedical imaging. Macroscopic data representing a volume of tissue is obtained. Photographic data representing cross-sections of the volume of the tissue is obtained. Microscopic data representing the cross-sections of the volume of the tissue is obtained. The microscopic data is registered to the photographic data. The macroscopic data is registered to the photographic data. An image is generated as a function of the microscopic data, macroscopic data, or both microscopic and macroscopic data. The image is generated as a function of the registering of the microscopic data to the photograph data and as a function of the registering of the macroscopic data to the photographic data.

In a second aspect, a system for biomedical imaging is provided. A memory is configured to store first data representing a tissue volume. The first data is from a microscopic imaging source. The memory is configured to store second data representing the tissue volume. The second data is from a macroscopic imaging source of a different type than the microscopic imaging source. The memory is configured to store third data representing the tissue volume. A processor is configured to spatially align the first data and the second data as a function of spatial alignments of the first data with the third data and the second data with the third data. The processor is also configured to render an image as a function of the first and second data and the spatial alignment of the first data and the second data. A display is operable to display the image of the tissue volume.

In a third aspect, a computer readable storage medium has stored therein data representing instructions executable by a programmed processor for biomedical study. The storage medium includes instructions for first registering macroscopic scan data of tissue at a first stage of processing with intermediate scan data of the tissue at an intermediate stage of the processing; second registering microscopic scan data of the tissue at a second stage of processing, the intermediate stage in between the first and second stages, the second registering occurring before, after, or while the first registering occurs; and spatially transforming between the microscopic and macroscopic scan data as a function of the first and second registrations.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Software determines relative spatial alignment of both microscopic and macroscopic medical imaging data for visualization, quantification, or other purposes. Microscopic and macroscopic medical imaging data are acquired from different sources. The microscopic and macroscopic datasets are registered. The registered data is used for viewing, manipulating, or navigating. For example, datasets associated with objects, structures, and/or function (e.g., labeled for a targeted protein) within the micro and macro datasets are selected. The dataset may be used for rendering at different resolution scales ("multi-resolution viewing").

Figure 1:
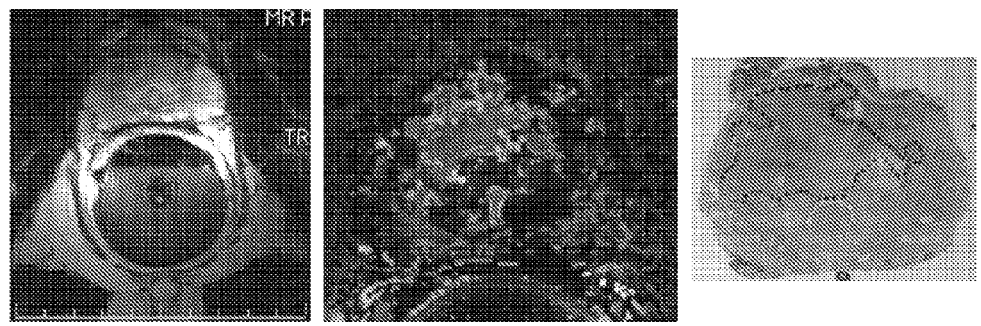
FIG. 1 shows example medical images of microscopic and macroscopic data.

FIG. 1 shows example medical images of the prostate. The left image is a T2-weighted MR image. The middle image is a 3T DCE-MR image using color mapping (shown in grayscale). The right image is a Hematoxylin-and-Eosin (H&E) stained whole mount with pathologist's delineation of a tumor. In this example, paired preoperative DCE-MRI and post-operative whole mounts of the prostate are used. The images are for a patient with pT3a Gleason score 7 (3+4) prostate cancer involving right>left lobe with ≈40% total involvement. Other conditions, organs, or types of images may be used.

The processing for obtaining the microscopic whole mount images may create relative artifacts, including fixation-induced shrinkage and non-linear tissue deformations that occur after tissue removal from the body (i.e., BPH nodule-induced tissue expansion). To limit registration difficulties due to the artifacts, the macroscopic and microscopic data are mapped to intermediary data. The mapping between the pre-operative macroscopic data and post-operative microscopic sections is divided into two steps: microscopic data (e.g., whole mount image)→digital photographs, and macroscopic data (e.g., DCE-MRI)→the digital photographs. The digital photographs are of the tissue in an intermediate state of processing, such as after removal from the patient and before slicing for mounting. By mapping both microscopic and macroscopic data to the digital photographs, the macroscopic and microscopic data may be aligned.

In other examples, the macroscopic data is acquired post-operative. Other types of intermediate data may be used, such as any of the macroscopic imaging data types. The co-registration algorithm does not require prostate- or prostate cancer-specific features. The spatial alignment is applicable to other cancers, organs, and/or conditions.

Figure 2:
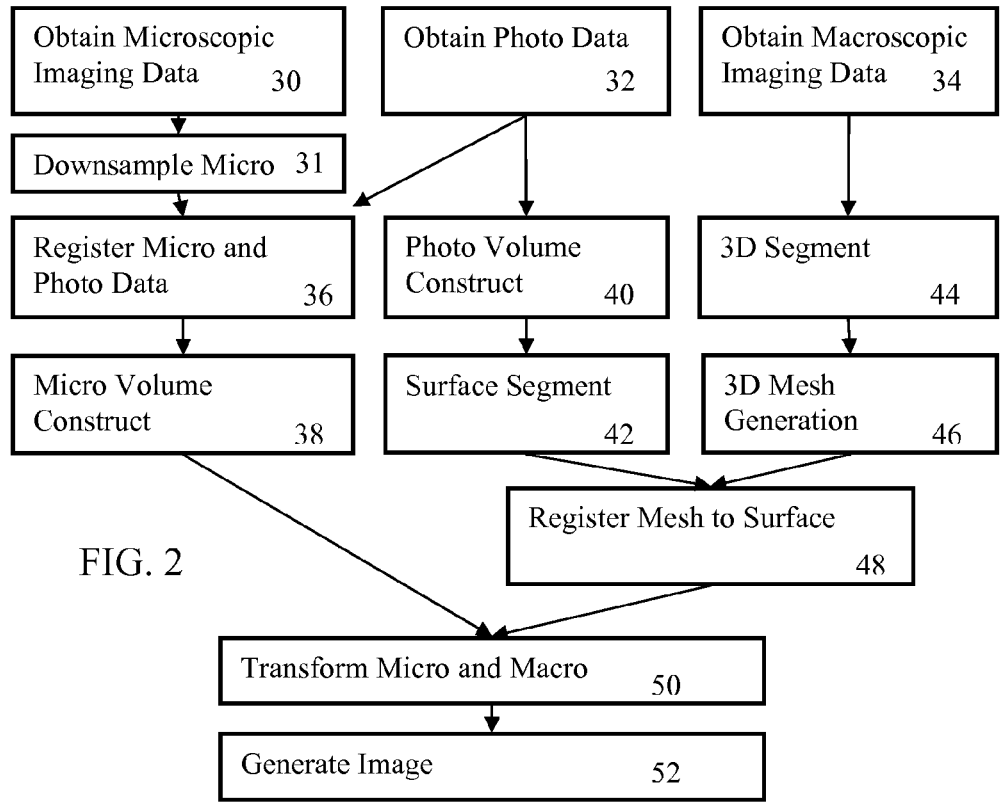
FIG. 2 is a flow chart diagram of one embodiment of a method for registering microscopic and macroscopic data in biomedical imaging.

FIG. 2 shows a method for biomedical imaging. The method is implemented by the system 60 of FIG. 4 or another system. The acts are performed in the order shown or other orders. For example, acts 40-48 are performed before acts 31, 36 and 38. Additional, different, or fewer acts may be provided. For example, act 31, 46, and/or 52 are not provided. The registrations of acts 36 and 48 occur at a same time (e.g., interleaved) or different times (e.g., act 36 is before or after act 48). Other acts are performed in parallel or sequentially.

In act 34, macroscopic data is obtained. The macroscopic data represents a volume of tissue. For example, the macroscopic data represents gross tissue structure or an organism, but not at cellular, sub-cellular, or molecular resolutions or of cellular structure. Expressed relatively, the macroscopic data has less resolution than microscopic data.

Macroscopic data is obtained with a different imaging modality than microscopic data. For example, the macroscopic data is image or scan data acquired using x-rays, ultrasound, magnetic resonance, photon emission, positron emission, or other radio frequency energy. Any now known or later developed type of scanning or mode may be used, such as computed tomography, magnetic resonance, x-ray, ultrasound, positron emission tomography, single photon emission tomography, or combinations thereof. The scan may be performed to better indicate function of the tissue, such as FDG imaging.

The macroscopic data is obtained from an imaging system. For example, 2D, 3D, and/or 4D image data is acquired in real-time from radiological equipment, such as CT, MR, micro-MR, PET, micro-PET, SPECT, SPECT-CT, ultrasound, or X-Ray systems. Alternatively, the macroscopic data is acquired from memory, such as from an image storage server or database. Either single or multi-modality (e.g., CT and MR) image data is acquired and stored for further registration with microscopic imaging data.

The macroscopic data represents a region of a patient, such as tissue and/or fluid. The region is a planar region (e.g., 2D) or a volume region (e.g., 3D). For example, macroscopic data spaced along a regular grid in three-dimensions is obtained. Alternatively, the data may be spaced according to a scan format or irregular grid. Due to the lesser resolution, the macroscopic data may represent a larger region than the microscopic data. In other embodiments, the macroscopic and microscopic data represent a same size region.

The macroscopic data is obtained for study of a specific patient, animal, and/or tissue. In one embodiment, the macroscopic data is acquired for study of a candidate drug. The data is pre-clinical data (i.e. animal imaging) or clinical data (human patients). The data represents a scan prior to and/or after exposure to the candidate drug. For example, the macroscopic data is acquired by scanning or imaging before and after exposure to the drug in order to determine the effects the drug may have had on tissue structure or function. As another example, the macroscopic data is obtained from a patient for diagnosis of a medical problem. The tissue is scanned while still within (e.g. internal organs) or on (e.g. skin) the patient (i.e., in vivo imaging). In the example of FIG. 1, the macroscopic data is obtained as MR data in viva In another example, the tissue is scanned outside of or after being removed/resected from a patient. The macroscopic data may be obtained by scanning frozen tissue, paraffin encased tissue, or tissue at another stage of processing after biopsy or resection.

The macroscopic data may be segmented to identify particular tissue structures, landmarks, or organs. Automated, semi-automatic, or manual segmentation may be used.

In one embodiment, fiduciary markers are provided by or in the scanned tissue or patient. The markers are positioned prior to acquisition of the macroscopic and microscopic data. Any fiduciary marker may be used, such as beads, buttons, or other materials selected to be responsive to the scan for macroscopic data. Alternatively, a lack of material may be used. For example, a fine needle creates holes through the region of interest.

The fiduciary markers are located to indicate position. For example, a line and a point, or three points are positioned for accurate orientation and registration of the region of interest. The markers are within the tissue, adjacent the tissue, or spaced from the tissue. For example, the markers are positioned on the skin of a patient (e.g., fluorescent spay paint). The macroscopic scan coordinate system is aligned with the markers or includes the markers for later alignment. In alternative embodiments, features within the tissue itself (e.g. blood vessels or other morphological landmarks) are used as markers. These tissue features assist with the registration instead of or in addition to fiduciary markers. In other embodiments, fiduciary markers or any other markers are not used.

In act 32, intermediary data is obtained. The intermediary data is scan or image data from a point in the tissue processing between the scan to acquire macroscopic data and the mounting to acquire microscopic data. For example, the tissue is removed from the patient, frozen, encased in paraffin, sequentially sliced, and the slices mounted. Other processing may be used, including different, additional, fewer stages. The intermediary data is obtained after removal and before mounting or intermediate to obtaining the macro and micro data.

Any type of imaging may be used to acquire the intermediary data, such as the modes or types mentioned for macroscopic scanning. The same or different mode than used for macroscopic scanning may be used. In one embodiment, optical scanning is used. For example, a photograph is acquired with or without magnification (e.g., block-face digital imaging prior to making the cut).

The intermediary data represents a one, two, or three-dimensional region of the tissue. The intermediary data has a same or different spatial extent and/or resolution as the macroscopic and/or microscopic data.

In one embodiment, photographic data is obtained. Digital or analog photography may be used. The photographs are taken as slices are cut for mounting. The cross-section of the tissue is photographed before slicing. For example, after each slice is cut, a photograph is taken of the block face or tissue exposed by removing the previous slice. The block face is on the remaining block of tissue still be sliced. After photographing, the next slice is removed, exposing another cross-section of block face for photographing. The photographs are obtained in vitro of a plurality of exposed cross-sections, providing data representing the volume of tissue during processing.

In act 30, microscopic data is obtained. Microscopic data represents micron or sub-micron levels of resolution. Microscopic data represents cellular or molecular information (i.e. structural or functional). The microscopic data may have a greater resolution than the macroscopic data.

The microscopic data represents a region of tissue. The region is a same region (e.g., volume) as for the macroscopic data, but may represent regions outside of the macroscopic scan or a sub-sized region. The region is a two or three-dimensional region. For example, data representing tissue along a regularly spaced or scan distributed three-dimensional grid is obtained. As another example, microscopic images are obtained for each of 3 mm or other thickness slices, providing microscopic data representing a volume. One or more images may be taken of each cross-section or mounting, such as tens or hundreds of images for sub-regions of each cross-section being stitched together to represent the entire cross-section.

Microscopic data is obtained with a microscope or other device for imaging at micron levels of resolution. Any modality may be used, whether now known or later developed. The modality used for acquiring the microscopic data may be a different mode than used for acquiring the macroscopic data.

In one example, histology and/or immunocytochemistry is performed on the appropriate region of interest. In the case of pre-clinical data, an animal is euthanized and perfused. For non-live preparations, the animal is typically fixed (e.g., with paraformaldehyde) before histological processing. In the case of clinical data, a patient's organ or tissue sample is usually either removed or biopsied, but "in vivo" (in living system) imaging (e.g. using fiber optic imaging methods) could also be used. Removed organs, such as a prostate, are further processed for histology. During histological processing, thick tissue sections (e.g. 50-100 microns) are cut along a desired planes (coronal, saggital or longitudinal) through the region of interest. The slices are imaged after slicing and/or mounting. The tissue section is alternatively oriented with respect to fiduciary markers, such as being parallel to a plane established by the markers, being through the markers, including the markers, or at a measured angle or position relative to the markers.

The prepared tissue is scanned or imaged to obtain the microscopic data. For example, digital microscopy is performed to obtain microscopic data representing the tissue region as a three-dimensional region. After stacking the images based on the thickness of the cut and the distance between the cuts, the microscopy data represents the three-dimensional region. The harvested tissue sections are scanned with a microscope. The microscope acquires 2D, 3D, and/or 4D microscopic data sets. In microscopy scans, data representing different planes throughout the tissue section are acquired. Other modalities, now known or later developed, may be used, such as a scanning electron microscope.

In one embodiment, one or more sets of the microscopic data are functional data. For example, the tissue is incubated with fluorescently labeled or chromogenically labeled antibodies. The antibodies are used to label the desired targets. For example, multiple fluorophores/chromophores label more than one functional structure of interest (i.e., multispectral imaging). The microscopic data may provide a more detailed representation of structural or functional information that was captured by related macroscopic data. For example, microscopic data may permit (sub-)micron resolution localization and visualization of radiopharmaceuticals or other imaging agents used in a macroscopic imaging procedure that have been taken up by, or are bound to, cells in the target area. The labeling co-localizes the cells with other sub-cellular components of interest (e.g. receptors, neurotransmitters, structural elements, etc.). Data for multiple images and/or volumes is acquired (e.g. one image or volume per fluorophore/chromophore). Alternatively, a single volume that contains the locations of multiple fluorophores/chromophores is obtained. In other embodiments, a single volume of single function data is obtained.

The microscopic data is obtained as "in vitro" or "in vivo" imaging data. The data is obtained from memory or in real time with scanning. The data represents the tissue before and/or after therapy, before and/or after exposure to a candidate drug, or after biopsy for diagnosis.

The microscopic data may represent fiduciary markers. For example, the fiduciary markers reflect the energy used to scan the tissue, such as being optically detectable. By sectioning the tissue to include the markers on or within the tissue, information representing the markers as well as the tissue is obtained. The fiducial markers may be used to align the planar images in a stack of the microscopic data representing the three-dimensional region. In alternative embodiments, the microscopic data does not represent the markers, such as where morphological features or speckle pattern are used for alignment.

In one embodiment, at least some of the microscopic data is scanned and/or prepared for registration. The data is different from data used for macro imaging or other purposes. For example, reference tissue sections are cut and exposed to a standard histological stain (e.g. hematoxylin and eosin), and digitized images of these sections are acquired at one or more magnifications (e.g. 100×, 400×, 1000×). The resulting microscopic data is used to provide structural reference for later registration of the microscopic data with the macroscopic data.

Acts 31, 36, and 38 provide registration of the microscopic data with the intermediary data. Additional, different, or fewer acts may be used, such as not performing acts 31 or 38. For example, the microscopic data is filtered to reduce aliasing effects prior to performing act 31.

In act 31, the microscopic data is down sampled. The microscopic data may be generated by stitching about 7000 or other number of individual microscopy pictures from a 2"×3" slide. FIG. 1 shows an example of the resulting stitched together image. This resolution is much greater than the resolution of the intermediary and/or macroscopic data. To avoid unnecessary processing, the resolution of the microscopic data is reduced. Prior to performing image co-registration, the super-resolution image is down-sampled to the same scale as that of the corresponding block face digital photograph or intermediary data. In alternative embodiments, the intermediate data is interpolated or up sampled. In other embodiments with or without up sampling and/or down sampling, the microscopic data and photographic data are at different resolutions for registration.

In act 36, the microscopic data is registered to the photographic data. The registration orients the coordinate systems for the different data. Either the microscopic data or the intermediary data may be used as a base reference to register the microscopic data to the photographic data. The registration is for translation and/or orientation in one, two, or three-dimensions. Any combination of translation and rotation degrees of freedom may be used, such as 6 degrees (3 axes of rotation and 3 axes of translation). Free form local deformations are specifically recovered. Global, local, rigid, non-rigid or any other now known or late developed registration may be used.

The data is registered using tissue landmarks (e.g. morphological features), fiduciary markers, sensor measurements, data matching, correlation, atlases, or combinations thereof. For example, tissue landmarks and/or fiduciary markers common to both of the intermediary data and microscopic datasets are aligned. As another example, the location of the microscopically scanned tissue relative to fiduciary markers is aligned relative to the locations of the fiduciary markers represented by the intermediary data. In another example, a stereotactic atlas or other atlas indicates the relative location of landmarks or other information represented by the microscopic data to an organ or structure represented by the intermediary data. Various types of atlas data (e.g. for brain, across different species) are available.

By searching through different translations, warpings, and/or rotations, the alignment with a highest or sufficient correlation is selected. Any search pattern may be used, such as numerical optimization, course-to-fine searching, subset based searching, or use of decimated data.

The correlation may be based on all of the data in the sets. Alternatively, the correlation is based on a sub-set. The subset may be the reference frames of microscopic data or data for at least one feature represented in the both types of data. For example, the user or a processor identifies features in each data set. The features may be tissue boundaries, tissue regions, bone region, fluid region, air region, fiduciary markers, combinations thereof, or other feature. The data representing the features with or without surrounding data is used for the correlation. The features may be identified in one set (e.g., microscopic) for matching with all of the data in another set (e.g., intermediary), or features of one set may be matched to features of another set.

The data may be used for correlation without alteration. In other embodiments, one or both sets of data are filtered or processed to provide more likely matching. Filters may be applied to highlight or select desired landmarks or patterns before matching. For example, higher resolution microscopic data is low pass filtered, decimated, or image processed to be more similar to intermediary data. As another example, gradients for each type of data are determined and matched.

In one embodiment, the microscopic and intermediary data both represent the same cross-sections. The data corresponding to a given cross-section is used to register for that cross-section in two-dimensions. The registration is performed for each cross-section. In other embodiments, the registration is performed for volume datasets or along one dimension.

A two-dimensional to two-dimensional non-rigid registration is performed for the cross-sections. The two-dimensional regions or datasets are spatially aligning with a two-dimensional non-rigid transform. The registration spatially aligns the microscopic images of mounted slices removed from the block face with the photographs of the block face prior to removal or slicing.

The non-rigid registration may be a 2D-2D mono-modal (e.g., optical images) intensity based deformable image registration technique. For example, local block matching using correlation, minimum sum of absolute differences or other approach is used. The optical slope is used and the local variation is limited to avoid discontinuous matches, such as with a spring or elastic cost function. The two digital images may have enough corresponding texture features, making the intensity-based registration possible. Rigid transforms may be used as an initial step to the non-rigid registration process.

The registration process is performed automatically. The automatic registration algorithm may also provide local confidence measures regarding the accuracy of the transformation map. In a semi-automatic approach, the user may intervene, such as adjusting the registration, where low confidence is indicated.

In another embodiment, two sets of corresponding features visible on both microscopy and photography sections are selected. These features may be selected based on natural saliency or even artificially marked by airbrushed or other fiducials applied prior to cutting. One set of features is used as "fiducials" and another set as "targets." To establish the lower bound for the target registration accuracy, landmark-based registration on the set of fiducials is provided. A transformation model, such as thin plane spline, is applied and the target registration error (TRE) on the set of targets points is computed. This target registration error is the baseline for the registration accuracy and incorporates various sources of error such as fiducial placement and their spatial distribution. The intensity-based registration is then performed by masking out the areas around the selected points and comparing the target registration error with the one computed as the results of the fiducial-based registration.

The appearance of the down-sampled histological slices may be quite different from the corresponding pre-cut photographs. This may cause difficulty for the 2D-2D free-form registration. Specific image similarity metrics that can cope with these radiometric variations may be used. For example, a texture metric or statistical variation metric is used. Furthermore, limiting the dimensionality of the deformation field may help with cases where the image contrast and textures cannot be robustly exploited for the registration purposes.

In act 38, a dataset representing the volume is constructed with the microscopic data. The microscopic data represents a plurality of two-dimensional cross-sections. Using the known thickness (3 mm plus blade width), a measured thickness, or other information, the microscopic data may be assembled into a volume dataset.

The volume dataset is assembled from transformed microscopic data. Using the registration, the microscopic data is transformed to the intermediary data frame as a reference. Alternatively, the volume dataset is assembled from non-transformed data, but a matrix, transformation cascade or other data indicates the spatial relationship between the microscopic volume dataset and the intermediary data domain.

Acts 40-48 provide registration of the macroscopic data with the intermediary data. Additional, different, or fewer acts may be used, such as not performing acts 40 or 46. In an alternative embodiment, a volume, planar, linear, or other region or regions of macroscopic data are matched to the intermediary data without segmentation. For example, tissue structures in one dataset are correlated with tissue structures in another dataset. In yet another alternative embodiment, the intermediary data and/or the macroscopic data are down sampled or up sampled to be at a same or closer resolution.

In act 40, a dataset representing the volume of tissue is constructed with the intermediary data. The reconstruction is the same or different than the reconstruction of act 38. The volume of transformed microscopic data from act 38 may be used as the intermediary data. The transformed microscopic data is in the intermediary data domain or coordinate system.

In one example embodiment, the photographic data represents different cross-sections of the tissue. Knowing, measuring, or estimating the tissue slice thickness is used to create a volume dataset from the photographic data. For example, the nominal thickness of the cuts (e.g., slices plus blade or saw width) is used to stack the photographic data representing each slice or block face. Correlation of tissue structure, markers, fiducials, or other information corrects for translational and rotational misalignments. In one embodiment, linear or other markers are arranged in the paraffin such that dots or other marks appear in the photographs. These markers may be used to determine rotation, twist, and/or translation to align the photographic data for stacking.

In act 42, the dataset of intermediary data, such as the photographic data, is segmented. The segmentation may identify a type of tissue from other tissues or materials, such as distinguishing the prostate from the paraffin. Alternatively or additionally, the segmentation may identify a surface, boundary, or other tissue structure.

Any now known or later developed segmentation may be used. The segmentation is automatic or semiautomatic. In alternative embodiments, manual segmentation is provided by the user tracing a boundary. In one embodiment, a surface segmentation is used. A surface mesh is generated from the 3D volume using a semi-automatic segmentation algorithm. For example, a multi-label random walker (MLRW) data segmentation algorithm uses a series of labeled seeds within the image or volume and automatically computes the boundaries that compartmentalize the data into regions corresponding to each set of seeds. The user selects one or more locations within the tissue and one or more location outside of the tissue of interest. The labels or seeds are in two groups, foreground (e.g., prostate tissue) or background (e.g., paraffin). A binary segmentation is output, identifying locations within the volume as in or out of the tissue of interest. A surface mesh is generated by identifying the boundary between the tissue of interest and other tissue or material.

In act 44, the macroscopic data is segmented. The macroscopic data represents a volume of tissue. Alternatively, a volume dataset is created by stacking planar scan data. In another embodiment, the macroscopic data is disassembled into planar regions, such as planar regions corresponding to the cross-sections of the intermediary data. Planar segmentation may be used.

The segmentation of macroscopic data is the same or different than the segmentation of the intermediary data in act 42. Where the macroscopic data is a different type of data than the intermediary data, different segmentation algorithms may be more appropriate. Any now known or later developed segmentation may be used, such as a surface segmentation. A macroscopic surface is segmented from the macroscopic scan data and for matching with an intermediate surface of the intermediate data.

In one embodiment, 3D segmentation is provided. In the prostate example, the prostate is segmented semi-automatically using a version of the random-walker based segmentation technique. Rather than requiring multiple seeds, a single seed approximately in the center of the tissue of interest is placed by the user. A prior statistical shape model of the prostate or other tissue structure is used with the seed to identify the tissue of interest. The range of intensities associated with the tissue of interest in a given imaging modality is known. This prior knowledge is used to identify the tissue of interest. The intensities of the tissue of interest are matched to the statistical model, such as using an intensity based registration. The result is identification of the tissue of interest using the statistical model.

In act 46, a three-dimensional mesh is generated. The segmented volume is used to compute a 3D volumetric mesh. Any mesh algorithm may be used, such as generating the mesh using a Delaunay-based or marching cube algorithm. The type of tissue is used to predict internal movement given movement of the external surface. The mesh allows prediction of internal deformation given surface deformation.

A surface mesh may be generated from a 3D volumetric mesh. Alternatively, the boundary of the tissue of interest is determined from the segmentation. The surface is used for registration.

In act 48, macroscopic scan data of tissue at a first stage of processing is registered with intermediate scan data of the tissue at an intermediate stage of the processing. For example, the macroscopic MR data is registered to the photographic data. The registration orients the coordinate systems for the different data. Either the microscopic data or the intermediary data may be used as a base reference to register the macroscopic data to the intermediary data.

Any now known or later developed registration may be used. For example, correlation or minimum sum of absolute differences is used to determine a rigid alignment of structures or other tissue information. The information used for matching and/or the information to be matched represents automatically or manually identified tissue structures, intensity patterns, or other information.

In one embodiment, a surface from the surface segmenting of the intermediary dataset is aligned with a surface from the surface segmenting of the macroscopic data. For example, a deformation of the mesh to match the intermediate surface with the macroscopic surface is calculated. Deforming the mesh to the intermediate surface spatially converts the macroscopic data to the coordinates of the intermediary data.

The deformation is a rigid registration in one embodiment. The macroscopic 3D mesh is aligned to the transformed microscopic or the photographic surface mesh by minimizing the average distance error between the surfaces meshes. For example, iterative closest point (ICP) or other surface alignment is used.

Alternatively or additionally, the deformation is non-rigid or a deformable registration. To account for deformations that might have happened during the resection process, a non-rigid approach is used. 3D mesh deformation and surface matching are performed. For example, a geometrically freeform transformation map is generated to link each pixel on the photographed section to the corresponding voxel in preoperative T2-weighted MRI and/or DCE-MRI (macroscopic data). An intensity-based method may be used. An intensity-based similarity metric, such as mutual information, should have at least statistical dependency between the corresponding intensity pairs from the two datasets or surfaces. In this case, surface meshes are converted to distance volumes, where zero indicates a point in the boundary, positive values indicate internal points distance to the boundary and negative values indicate external points distance to the boundary.

Machine learning algorithms may be used to determine the match. Learning algorithms rely on feature sets that are primarily derived from intensities. If one uses the very same intensity spatial groups (volume) for registration, then the chosen similarity may dictate the mapping result. To avoid these concerns, a surface-based method that minimizes the surfaces distances and generates deformation on the boundaries of the object is used. Concurrently, an established nominal mechanical tissue properties of prostate are used to propagate the deformation within the volume enclosed by the surface mesh. The process of moving the boundaries and propagation of the deformation field inwards is formulated as an optimization problem and solved efficiently using finite element modeling.

In one embodiment, surface matching is not used or the datasets are aligned prior to surface matching. The data of the tissue of interest is correlated or registered independent of the surfaces. For the 3D-3D registration between the macroscopic data and 3D reconstructed photographs, natural landmarks, expert visual evaluations, speckle, or other tissue matching may be used. Artificial landmarks are not used. Alternatively, artificial landmarks are used.

Corresponding landmarks are identified on the 3D photographic dataset and the 3D macroscopic dataset. For the prostate, the most apparent landmark may be the urethra across various slices, visible in both datasets. Any number of landmarks may be used, such as five to ten corresponding landmarks.

For the 3D-3D deformation mesh registration, sensitivity to the choice of the material properties of the prostate or other tissue may cause error. The assumption of uniform or constant mechanical tissue property might not hold. To address these issues, the mechanical properties of the prostate or tissue are updated according the pre-operative MR or other images. Inhomogeneity of the material property parameters may be built into the registration or mesh deformation formulations. This may result in a more complicated optimization problem. Graphics processing units with a set of parallelized processing engines may optimize more efficiently or quickly.

In act 50, spatial transformation occurs between the microscopic and macroscopic scan data as a function of the registrations of acts 36 and 48. Rather than registering the macroscopic data to the microscopic data directly, two or more stages of registration are performed. The macroscopic and microscopic data are registered to intermediary data. This registration occurs with both the micro and macro to the intermediary or occurs with one of the macroscopic or microscopic data registered to intermediary data and then registered again to the other of the microscopic or macroscopic data.

The transformation occurs as reformatting the data to a common coordinate system. Alternatively, the transformation is a matrix, transform cascade or other data indicating a spatial relationship between locations represented by different datasets. Mapping both 3D microscopic and 3D macroscopic data to the digital photographs or other intermediary data creates a transformation (i.e. mapping) cascade that can be used to bring the datasets into alignment.

Using the transformation, the 3D datasets may be fused together. The microscopic and macroscopic scan data are fused into a dataset as a function of the spatially transforming. Any combination may be used, such as averaging, weighted averaging, mapping different display characteristics to each type of data (e.g., grayscale to the macroscopic data and color to the microscopic data), or other combination may be used. The spatial alignment is used to form one set of data. The resolution in the fused data set may vary, such as having higher resolution for the region associated with the microscopic data. Alternatively, the spatial relationship of the macro and microscopic datasets is used, but with separately stored data sets.

One alignment may be used for other combinations of data. For example, both CT and MR macroscopic datasets are obtained. If the coordinate systems are the same or have a known relationship, the alignment of the CT data with the microscopic data may also be used to indicate the alignment for the MR macroscopic data with the microscopic data. The alignment of data acquired with no or one type of labeling (e.g., stain, imaging agent, biomarker, or other functional indicator) may be used to align datasets acquired with other types of labeling.

In act 52, the fused dataset or separate datasets are volume rendered. An image is generated as a function of the microscopic data, macroscopic data, or both microscopic and macroscopic data.

Any type of rendering may be used. The image is a two-dimensional representation rendered from data representing a volume. Any type of three-dimensional rendering may be used, such as surface or projection rendering. Any type of blending or combination data may be used. Alternatively or additionally, a two-dimensional image representing a plane or surface is generated. Data along or near the plane may be interpolated or selected, allowing generation of an image representing any arbitrary plane through a volume. A multiplanar reconstruction may be generated. Images for fixed planes, such as associated with a plane defined by fiduciary markers, may be generated.

The transformation may be used to scale or otherwise alter the volume rendering of the separate datasets to visually depict the tissue in a same or similar spatial frame of reference. The volume rendering is a function of the spatial transform, either by rendering from transformed data, rendering from the fused dataset, or rendering using the transform. The rendering is a function of the registering of the microscopic data to the intermediary data and as a function of the registering of the macroscopic data to the intermediary data. The image is generated as a function of the spatial aligning of acts 38 and 48. The spatial alignment allows indication of the position of the microscopic data relative to the macroscopic data. For example, an overlay or more opaque region in an image generated from macroscopic data indicates the relative location of available microscopic data.

The spatial alignment allows generation of the image from both types of data. For example, the macro and micro data are interpolated and/or decimated to a same or similar resolution. The image is generated using both types of data. The data may be relatively weighted, such as by assigning an opacity value. The different types of data may be rendered differently and overlaid with each other. The different types of data may be used for different pixel characteristics, such as macroscopic data indicating intensity and microscopic data indicating color or shade. The spatial alignment determines which values represent which voxel or spatial locations.

The transformation permits rapid identification and quantification of volumes of interest (VOIs). A volume of interest in one image may be transformed or related to corresponding locations in another image. The histological slices may be displayed unprocessed. The computed deformation fields are used to warp and overlay the markings on the slices onto pre-operative DCE-MR data.

In one embodiment, any now known or later developed multi-resolution imaging may be provided. Multi-resolution, multi-scale imaging visualizes the fused data at different zoom levels. At the macroscopic level, the microscopic image or volume data is overlaid or included in the form of a rectangular sub-region at the appropriate position and orientation. As the user zooms into the region of the microscopic sub-region, the surrounding macroscopic image or volume data is visualized together with the surrounding anatomical landmarks. The microscopic image or volume detail is progressively increased when zooming. A variable level of detail rendering may permit visualization between microscopic and macroscopic scales, allowing the user to view relative differences and effects at different scales of a given drug, disease, and/or therapy.

In an alternative embodiment, a wire frame or graphic represents the microscopic region in an image from the macroscopic data. A separate microscopic image is generated for the microscopic region. For three-dimensional rendering, the projection or viewing direction is the same or different for both images. Alternatively, the spatial alignment is used to overlay rendered or generated images.

Using the image or a sequence of images, the user may navigate to better identify a region of interest. After an image is generated, the user may indicate a different viewing direction, zoom level, opacity weighting, and/or other rendering parameter. Subsequent images are generated based on the changes. The user may navigate to more closely examine are given region, such as zooming into view a smaller region at greater detail. The image generation may access sub-sets of data as needed based on the navigation to limit processing and/or transfer bandwidth. As the user navigates to different zoom levels and/or sub-regions, the data appropriate for the zoom level and sub-region is used to generate the image. Different zoom levels may correspond to different relative amounts of the microscopy and macroscopy scan data. For example, a low-resolution image may use mostly macroscopic data with microscopic data being used to render a small section. A high-resolution image zoomed to the microscopic scan region may use mostly microscopic data with low opacity macroscopic data indicating surrounding tissue. Other levels of zoom may use equal or different amounts of the macro and microscopy scan data depending on the size and relative position of the imaged region of interest to the microscopic scan region.

The fused dataset or the transform may be used to calculate one or more quantities. Any quantity may be determined. For example, area, volume, number of voxels, average, variance, statistical value, or other value is determined. The data may be filtered to better highlight or emphasize values representing the desired characteristic for quantification. Any now known or later quantification may be used. The same or different quantities are calculated from the macroscopic and microscopic data.

The quantities are determined from the microscopy scan data. Quantities may be determined from macroscopy data. The registration of the macroscopy and microscopy data may be used to determine the region of interest for which the quantities are calculated.

Any one or more acts may be repeated. The repetition occurs at different times. For example, macroscopic and microscopic data is obtained and aligned before and after exposure of tissue to a drug. The repetition allows for temporal correlation. The change or progression of disease (e.g., before and after therapy) and/or reaction to drug exposure may be determined at macro and microscopic levels.

The temporal correlation may be indicated by change or difference between the same quantity calculated for different times. For example, a volume or average intensity associated with a labeled function is calculated from data representing tissue prior to exposure to a drug and from data representing tissue after exposure to the drug. A time series of values may be determined to show progression. Correlation analysis between microscopic and macroscopic data may also be provided.

Figure 3:
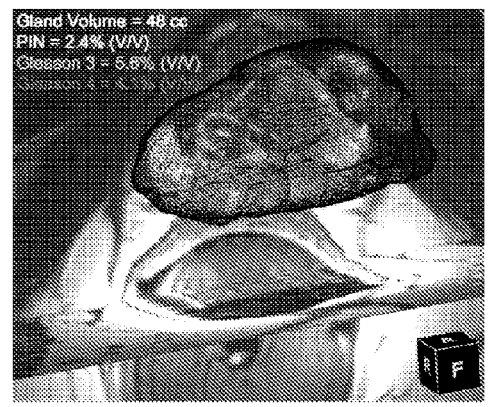
FIG. 3 illustrates an example image rendered from fused macroscopic and microscopic data.

FIG. 3 shows an example rendered image for the prostate. A whole organ image is rendered from the macroscopic data. This rendering is the oval shaped structure floating above the cut-planes (vertical and horizontal) rendered from microscopic data. Color is overlaid on the whole organ or macroscopic rendering. The color is coded as shades of yellow for prostatic intraepithelial neoplasia, green for Gleason grade 3 adenocarcinoma, and red for Gleason grade 4 adenocarcinoma. FIG. 3 also shows the results of quantifications.

Figure 4:
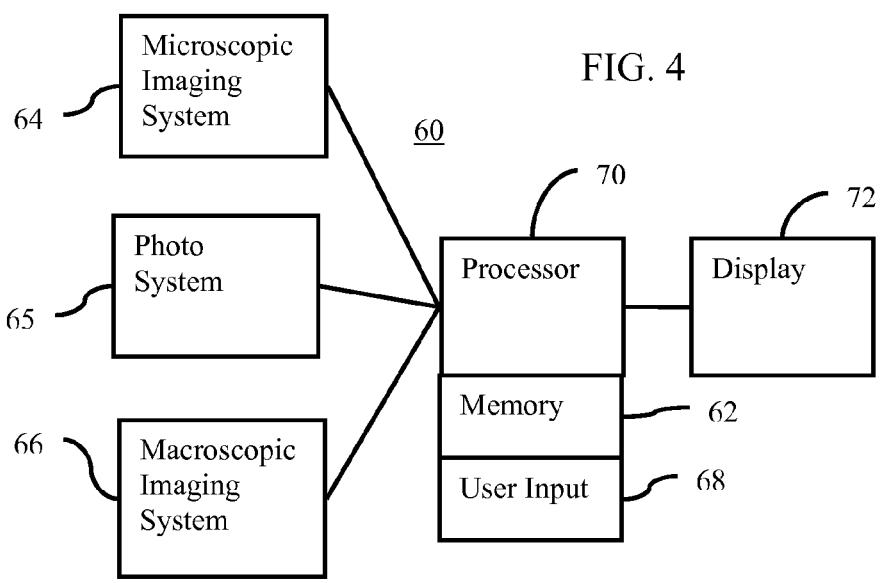
FIG. 4 is a block diagram of one embodiment of a system for biomedical imaging and/or study.

FIG. 4 shows a system 60 for medical or biomedical imaging. The system 60 includes a memory 62, a microscopy system 64, a photo system 65, a macroscopy system 66, a user input 68, a processor 70, and a display 72. Additional, different, or fewer components may be provided. For example, a network or network connection is provided, such as for networking with a medical imaging network or data archival system. As another example, additional macroscopy and/or microscopy systems are provided. In another example, the microscopy, macroscopy, and/or photo systems 64, 65, 66 are not provided. The marcroscopy, microscopy, and intermediary data are stored in the memory 62. In other example embodiments, the photo system 65 is a different type of imaging system.

The processor 70, user input 68, and display 72 are part of a medical imaging system, such as the diagnostic or therapy ultrasound, fluoroscopy, x-ray, computed tomography, magnetic resonance, positron emission, or other system. Alternatively, the processor 70, user input 68, and display 72 are part of an archival and/or image processing system, such as associated with a medical records database workstation or server. In other embodiments, the processor 70, user input 68, and display 72 are a personal computer, such as desktop or laptop, a workstation, a server, a network, or combinations thereof. The memory 62 is part of the workstation or system or is a remote database or memory medium.

The user input 68 is a keyboard, button, slider, knob, touch screen, touch pad, mouse, trackball, combinations thereof, or other now known or later developed user input device. The user input 68 receives user indication of interaction with a user interface. The user may select data, control rendering, control imaging, navigate, cause calculation, search, or perform other functions associated with using, imaging, and/or registering of macroscopic and microscopic data.

The memory 62 is a graphics processing memory, a video random access memory, a random access memory, system memory, random access memory, cache memory, hard drive, optical media, magnetic media, flash drive, buffer, database, server memory, combinations thereof, or other now known or later developed memory device for storing data or video information. The memory 62 is part of an imaging system, part of a computer associated with the processor 70, part of a database, part of an archival system, part of another system, or a standalone device. The memory 62 is configured by the processor 70 or software to store data.

The memory 62 stores datasets representing two-dimensional planes and/or three-dimensional tissue volume. The tissue volume is a region of the patient or animal, such as a region within the chest, abdomen, leg, head, arm, or combinations thereof, or a region of biopsied or harvested tissue. The tissue volume is a region scanned by a medical imaging modality. Different modalities or even scans with a same modality may be of a same or different size regions with or without overlap. The data may represent planar (2D), linear (1D), point, or temporal (4D) regions for one or more datasets.

At least one set of data is data from a microscopic imaging source, such as the microscopic system 64. The microscopic system 64 is a microscope, confocal microscope system, or other now known or later developed microscopic imaging system. The microscopic data includes images of mounted slices removed from a block face.

At least one set of data is data from an intermediary imaging source, such as the photo system 65. The photo system 65 is a digital camera, infrared camera, microscope, or other now known or later developed photographic imaging system. Other types of imaging may be used, such as ultrasound, x-ray, MR, CT, PET, or SPECT. The photo system 65 is a different type and/or mode of scan than used by the microscopic and/or macroscopic systems 64, 66, but may be a same type and/or mode. The intermediary data includes images, such as photographs of tissue cross-sections of a block face from before each slice is removed for mounting. Each block face corresponds to exposed tissue of the tissue volume.

At least one set of data is data from a macroscopic imaging source, such as the macroscopic system 66. The macroscopic system 66 is an ultrasound, x-ray, MR, CT, PET, SPECT, or other now known or later developed macroscopic imaging system. The macroscopic system 66 is different than the microscopic system, so that the data are from different modalities and/or imaging sources. The macroscopic data includes scan data from the tissue volume prior to any slicing for microscopic imaging.

The macroscopic, microscopic and/or intermediary data represent the tissue prior to, after, and/or during treatment, drug exposure, and/or disease. The microscopic data has a greater resolution than the macroscopic data. Any relative differences in resolution may be provided. Due to the differences in resolution, the macro and microscopic data represent tissue structure at different levels. The macroscopic data represents the tissue at a larger structure level than the microscopic data. The intermediary data is intermediate in stage of tissue processing, resolution, other relative difference, or combinations thereof.

The data is in any format. For example, each data set is interpolated or converted to an evenly spaced three-dimensional grid or is in a scan format at the appropriate resolution. Different grids may be used for data representing different resolutions. Each datum is associated with a different volume location (voxel) in the tissue volume. Each volume location is the same size and shape within the dataset. Volume locations with different sizes, shapes, or numbers along a dimension may be included in a same dataset. The data coordinate system for each type of data represents the position of the scanning device relative to the patient.

In one embodiment, one or more microscopic and/or macroscopic datasets include labeled tissue function information. The scan and/or processing of the data are performed to isolate, highlight, or better indicate tissue structure, locations, or regions associated with a particular function. For example in fluoroscopic imaging, an imaging agent (e.g., fluorescent dye) may be injected into a patient. The imaging agent provides a detectable response to x-rays. By flowing through the circulatory system, the imaging agent may provide detectable response highlighting the circulatory system, such as the vessels, veins, and/or heart. As another example, multispectral digital microscopic imaging generates a plurality of data sets each representing different structural or functional aspects associated with the tissue. Molecular level labeling may be used, such as exposing the tissue to fluorescently or chromogenically labeled antibodies designed to bind to particular cellular or tissue structure or proteins. These antibodies are designed to be visible in the scanning method.

The memory 62 or other memory is a computer readable storage medium storing data representing instructions executable by the programmed processor 70 for biomedical or medical study, such as registering, quantifying, and/or imaging. The instructions for implementing the processes, methods, approaches, and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 70 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for determining position, registering, quantifying, and/or generating images. The processor 70 is a single device or multiple devices operating in serial, parallel, or separately. The processor 70 may be a main processor of a computer, such as a laptop or desktop computer, or may be a processor for handling some tasks in a larger system, such as in an imaging system.

The processor 70 loads the data. Depending on the zoom level of the image to be rendered, the processor 70 loads the appropriate data. For example, all or a sub-sampling of the macroscopic data is loaded for little to no zoom levels. Microscopic data may be loaded for such zoom levels. For greater levels of zoom, only the sub-set of macroscopic data within a zoomed region is loaded. The microscopic data is loaded for zoom levels for which the microscopic data contributes to the rendering. Sub-samples may be loaded to avoid transfer bandwidth or processing bandwidth burden. Any multi-resolution imaging and associated data loading may be used.

The processor 70 also loads the intermediary, microscopic and macroscopic data for registering. Reference data, rather than an entire set of data, may be loaded and used for registering. Alternatively, entire datasets are used. The spatial alignment in rotation, translation, and/or warping of the macroscopic and microscopic data is determined. The alignment is determined using the intermediary data. Rather than one registration, two or more registrations are performed.

The registrations are performed as a function of tissue structure represented in both types of data, fiduciary markers represented in the both types of data, functional pattern represented in both types of data, atlas information, or combinations thereof. For example, similarities between the microscopic data or the macroscopic data and the intermediary data are identified. As another example, similarities between the micro or macro data registered to the intermediary data and the other of the macro or micro data are identified. Image processing may identify features. The user may identify features. Identifying three or more features or one or more features with a corresponding orientation represented by both data sets indicates relative positioning of the volumes.

Alternatively, similarity is determined using a correlation, such as a minimum sum of absolute differences, cross correlation, autocorrelation, or other correlation. For example, a two or three-dimensional set of data is translated and/or rotated into various positions relative to another set of data. The relative position with the minimum sum or highest correlation indicates a match, alignment, or registration location. The set of data may be sub-set, such as a region of interest or a decimated set, or may be a full set. The set to be matched may be a sub-set or full set, such as correlating a decimated region of interest sub-set of microscopic data with a full set of intermediary data or macroscopic data registered to the intermediary data.

Any rigid or non-rigid transform may be used. The spatial alignment of the macro and micro data to each other is based on the spatial alignment of each to the intermediary data. The spatial alignment is performed automatically or without user guidance. Alternatively, the user input 18 receives seed positions or other information for semi-automatically aligning.

The relative positioning indicates a translation, warping, and/or rotation of one set of data relative to another set of data. The coordinates of the different volumes may be aligned or transformed such that spatial locations in each set representing a same tissue have a same or determinable location. The registration for one set of microscopic data with macroscopic data may indicate the registration for other sets of the microscopic and/or macroscopic data.

The processor 70 is operable to render an image as a function of the registered data. Any type of rendering may be used, such as surface rendering, multi-planar reconstruction, projection rendering, and/or generation of an image representing a plane. For example, the image is generated as a rendering of or an arbitrary plane through the tissue volume. The image includes values for pixel locations where each of the values is a function of one or both of macro and microscopic data. For example, the macroscopic data is interpolated to a higher resolution and the microscopic data is decimated to a lower resolution such that the two resolutions match. The image is generated from both types of data. The image may be a volume rendering of or an arbitrary plane through the tissue volume.

The image is rendered based on user selection of the type of data. Where datasets corresponding to different or no structural or functional labeling are available, the user may select the dataset to be used for imaging. The dataset may be the same or different from the data used for registration.

The image is generated as a function of the zoom level. The user or the processor 70 indicates the zoom level. The data appropriate for that zoom level is selected and used for generating the image using any now known or later developed multi-resolution imaging.

Where both macro and microscopic data are used to generate the image, the types of data are blended. The blending may be a function of the zoom level. For example, greater zoom levels may emphasize the microscopic data, weighting the macroscopic data with a lesser weight.

Spatially aligned data may be combined, such as by summing, averaging, alpha blending, maximum selection, minimum selection or other process. The combined data set is rendered as a three-dimensional representation. Separate renderings may be used, such as laying a microscopic rendering over a macroscopic rendering. The combination provides feedback about relative position of the microscopic data to the larger macroscopically scanned region.

The processor 70 may calculate quantities. Modeling and/or machine learning associated with the registered data may be performed by the processor 70.

The display 72 is a monitor, LCD, projector, plasma display, CRT, printer, or other now known or later developed devise for outputting visual information. The display 72 receives images, graphics, or other information from the processor 70, memory 62, microscopic system 64, photo system 65, or macroscopic system 66. The display 72 displays the images of the tissue volume.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for biomedical imaging, the method comprising:
    obtaining macroscopic data representing a volume of tissue;
    obtaining photographic data representing cross-sections of the volume of the tissue;
    obtaining microscopic data representing the cross-sections of the volume of the tissue;
    registering, with a processor, the microscopic data to the photographic data with a first transform of coordinate systems for the microscopic data and the photographic data;
    registering, with the processor, the macroscopic data to the photographic data with a second transform of coordinate systems for the macroscopic data and the photographic data; and
    generating, on a display, an image as a function of the microscopic data, macroscopic data, or both microscopic and macroscopic data and as a function of the registering of the microscopic data to the photograph data and as a function of the registering of the macroscopic data to the photographic data;
    wherein obtaining the macroscopic data comprises obtaining in vivo imaging data of the tissue, wherein obtaining the photographic data comprises photographing the cross-sections of the tissue in vitro prior to slicing, and wherein obtaining the microscopic data comprises obtaining in vitro imaging data of slices after slicing.

2. The method of claim 1 wherein obtaining microscopic data comprises obtaining digital microscopy data from mounts of the tissue in slides, the mounts corresponding to the cross-sections of the volume.

3. The method of claim 1 wherein obtaining macroscopic data comprises obtaining computed tomography data, magnetic resonance data, positron emission tomography data, single photon emission tomography data, or combinations thereof.

4. The method of claim 1 wherein obtaining microscopic and macroscopic data comprises obtaining data with different imaging modalities, the imaging modality for the microscopic data having cellular, sub-cellular or molecular level resolution for the tissue and the imaging modality for the macroscopic data having a less resolution associated with tissue structure without cellular or more detailed structure.

5. The method of claim 1 further comprising:
constructing a dataset representing the volume with the photographic data;
surface segmenting the dataset; and
surface segmenting the macroscopic data;
wherein registering the macroscopic data to the photographic data comprises aligning a first surface from the surface segmenting of the dataset with a second surface from the surface segmenting of the macroscopic data.

6. The method of claim 1 wherein generating the image comprises three-dimensionally rendering the image from the macroscopic and microscopic data as a function of a spatial mapping based on the registrations.

7. The method of claim 1 wherein generating the image comprises fusing the macroscopic data with the microscopic data into a dataset and rendering the image from the dataset.

8. The method of claim 1 wherein obtaining the photographic data comprises obtaining after removal of the tissue from a patient.

9. The method of claim 1 wherein obtaining the microscopic data comprises obtaining after removal of the tissue from the patient.

10. The method of claim 1 wherein obtaining the photographic data comprises obtaining at an intermediary stage of processing the tissue for obtaining the microscopic data, the processing including removal from the patient, cross-sectioning, and mounting in slides, the intermediary stage occurring before the mounting in the slides and the obtaining of the microscopic data occurring after the mounting in the slides.

11. A method for biomedical imaging, the method comprising:
obtaining macroscopic data representing a volume of tissue;
obtaining photographic data representing cross-sections of the volume of the tissue;
obtaining microscopic data representing the cross-sections of the volume of the tissue;
registering, with a processor, the microscopic data to the photographic data with a first transform of coordinate systems for the microscopic data and the photographic data;
registering, with the processor, the macroscopic data to the photographic data with a second transform of coordinate systems for the macroscopic data and the photographic data; and
generating, on a display, an image as a function of the microscopic data, macroscopic data, or both microscopic and macroscopic data and as a function of the registering of the microscopic data to the photograph data and as a function of the registering of the macroscopic data to the photographic data;
wherein obtaining macroscopic data comprises obtaining in vivo magnetic resonance data, wherein obtaining photographic data comprises digitally photographing the cross-sections as block faces of the tissue prior to slicing off each block face, and wherein obtaining the microscopic data comprises obtaining the in vitro imaging data from mounts of the slices in slides.

12. A method for biomedical imaging, the method comprising:
obtaining macroscopic data representing a volume of tissue;
obtaining photographic data representing cross-sections of the volume of the tissue;
obtaining microscopic data representing the cross-sections of the volume of the tissue;
registering, with a processor, the microscopic data to the photographic data with a first transform of coordinate systems for the microscopic data and the photographic data;
registering, with the processor, the macroscopic data to the photographic data with a second transform of coordinate systems for the macroscopic data and the photographic data;
generating, on a display, an image as a function of the microscopic data, macroscopic data, or both microscopic and macroscopic data and as a function of the registering of the microscopic data to the photograph data and as a function of the registering of the macroscopic data to the photographic data; and
down sampling the microscopic data, wherein registering the microscopic data to the photographic data comprises performing a two-dimensional to two-dimensional non-rigid registration for the cross-sections, and further comprising constructing a dataset representing the volume with the microscopic data.

* * * * *